United States Patent [19]

Gosteli et al.

[11] 4,089,960
[45] May 16, 1978

[54] ANTIEMETIC, PSYCHOSOMATIC AND ANTIPSYCHOTIC HETEROCYCLIC PYRIDINE CARBOXAMIDES

[75] Inventors: Jacques Gosteli, Basel; Angelo Storni, Rheinfelden; Armin Züst, Birsfelden, all of Switzerland

[73] Assignee: Ciba-Geigy Corporation, Ardsley, N.Y.

[21] Appl. No.: 723,125

[22] Filed: Sep. 14, 1976

[30] Foreign Application Priority Data

Sep. 25, 1975   Switzerland ................ 12435/75

[51] Int. Cl.² ............................................ A61K 31/455
[52] U.S. Cl. ............................ 424/266; 260/293.53; 260/293.69; 260/293.87; 260/294.8 R; 260/294.9; 260/295 R; 260/295 AM; 260/295.5 R; 260/295.5 A; 260/326.85
[58] Field of Search ............. 260/295.5 A, 295 AM, 260/293.53, 293.69, 294.8 R, 294.9; 424/266

[56] References Cited

U.S. PATENT DOCUMENTS

| | | | |
|---|---|---|---|
| 2,748,134 | 5/1956 | Stoll et al. | 260/294 |
| 3,105,072 | 9/1963 | Felder et al. | 260/247.2 |
| 3,933,830 | 1/1976 | Barth et al. | 260/293.52 |
| 3,970,663 | 7/1976 | Regnier et al. | 260/295.5 A |

FOREIGN PATENT DOCUMENTS

| | | | |
|---|---|---|---|
| 2,162,917 | 9/1972 | Germany | 260/559 S |
| 2,327,193 | 1/1974 | Germany | 260/326.47 |
| 2,327,414 | 12/1973 | Germany | 260/293.77 |
| 2,452,405 | 5/1975 | Germany | 260/293.73 |

OTHER PUBLICATIONS

Kushner, S. et al, J. Org. Chem., 13, 834 (1948).

*Primary Examiner*—Henry R. Jiles
*Assistant Examiner*—Richard A. Schwartz
*Attorney, Agent, or Firm*—John J. Maitner

[57] ABSTRACT

The present invention provides new basically substituted pyridinecarboxamides having the formula I

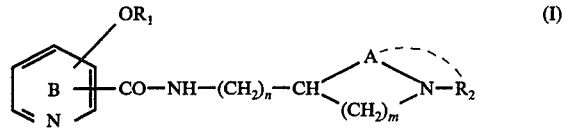

wherein
$R_1$ represents lower alkyl and $—OR_1$ is in the adjacent position to the carboxamide group,
$R_2$ represents lower alkyl or an ethylene radical which is attached to one of the trivalent radicals designated as A and the nitrogen atom located between it to form a 6-membered ring,
A represents a divalent saturated hydrocarbon radical which encompasses at most a single ring with 5 or 6 ring members and contains not more than 7 carbon atoms and whose two linkage positions are separated by (3–m) to 4 carbon atoms, or, if $R_2$ is an ethylene radical, represents the 1-propanyl-3-ylidene radical, if $m$ s 1, or the 1,2,4-butane-triyl radical, if $m$ is 0, and one of the factors $m$ and $n$ is 0 and the other is 1, and, if desired, the ring B is further substituted, and the acid addition salts of the compounds of the formula I. These new substances possess useful pharmacological properties, in particular antiemetic, psychosomatic and antipsychotic activity and can be used for the treatment of thought disturbances and of states of psychomotor excitation. Specific embodiments are N-[(1-ethyl-2-pyrrolidinyl)-methyl]-2,6-dimethoxynicotinamide and the pharmaceutically acceptable acid addition salts thereof.

21 Claims, No Drawings

ANTIEMETIC, PSYCHOSOMATIC AND ANTIPSYCHOTIC HETEROCYCLIC PYRIDINE CARBOXAMIDES

DETAILED DESCRIPTION

The present invention provides new basically substituted pyridinecarboxamides, and their addition salts, pharmaceutical compositions which contain the new substances and the therapeutic use of the new substances.

The basically substituted pyridinecarboxamides according to the invention have the formula I

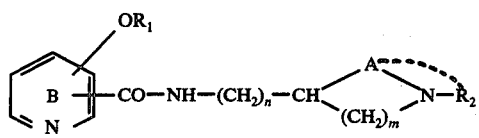

wherein
$R_1$ represents lower alkyl and $-OR_1$ is in the adjacent position to the carboxamide group,
$R_2$ represents lower alkyl or an ethylene radical which is attached to one of the trivalent radicals designated as A and the nitrogen atom located between it to form a 6-membered ring,
A represents a divalent saturated hydrocarbon radical which encompasses at most a single ring with 5 or 6 ring members and contains not more than 7 carbon atoms and whose two linkage positions are separated by $(3-m)$ to 4 carbon atoms, or, if $R_2$ is an ethylene radical, represents the 1-propanyl-3-ylidene radical, if $m$ is 1, or the 1,2,4-butane-triyl radical, if $m$ is 0,
and one of the factors $m$ and $n$ is 0 and the other is 1, and, if desired, the ring B can be further substituted. It is also an object of the invention to provide the acid addition salts of the compounds of the general formula I, in particular the pharmaceutically acceptable acid addition salts.

In the compounds of the general formula I, lower alkyl represented by $R_1$ and $R_2$ contains not more than 7, preferably not more than 4, carbon atoms, and is for example pentyl, iso-pentyl, hexyl, heptyl, and preferably propyl, butyl or iso-butyl. As $R_1$, lower alkyl is in particular ethyl and most preferably methyl, and as $R_2$ is in particular methyl and, most preferably, ethyl. A is a divalent saturated aliphatic hydrocarbon radical, for example 1- or 2-methyltrimethylene, tetramethylene and primarily trimethylene, or, if $m$ is 1, propylene and, most preferably, ethylene. A is also a divalent saturated cycloaliphatic radical, for example 1,3- or 1,4-cyclohexylene, or, if $m$ is 1, 1,2-cyclopentylene or, in particular, 1,2-cyclohexylene, or is a corresponding cycloaliphatic-aliphatic radical, such as 1,2-cyclopentylene-1-methylene or, in particular, 1,2-cyclohexylene-1-methylene. Where an ethylene radical $R_2$ is present, the appropriate 1-propanyl-3-ylidene radical is preferably attached in its 1-position to the ring nitrogen atom, or the appropriate 1,2,4-butanetriyl radical is preferably attached in its 4-position to the ring nitrogen atom and in its 1-position to the CH group in formula I, i.e. a corresponding basic radical attached to the amide group is in particular a (3-quinuclidinyl) or a [(2-quinuclidinyl)methyl] radical.

If desired, the ring B is substituted for example by lower alkyl, lower alkoxy or lower alkylthio, such as methyl, ethyl, propyl, iso-propyl, butyl, or methoxy, ethoxy, propoxy, iso-propoxy, butoxy, iso-butoxy or methylthio or ethylthio; halogen with an atomic number up to 35; lower alkylsulphinyl or lower alkylsulphonyl, such as methylsulphinyl, ethylsulphinyl, or methylsulphonyl or ethylsulphonyl; nitro; unsubstituted or mono- or disubstituted amino, such as amino, mono- or di-lower alkylamino or polymethylenimino, for example methylamino, ethylamino, propylamino, iso-propylamino, butylamino, iso-butylamino or dimethylamino, diethylamino or 1-pyrrolidinyl or piperidino or morpholino; sulphamoyl and mono- or disubstituted sulphamoyl, such as mono- or di-lower alkylsulphamoyl, for example methylsulphamoyl, ethylsulphamoyl, dimethylsulphamoyl, or diethylsulphamoyl, or by cyano. Lower alkyl, preferably methyl, or halogen with an atomic number up to 35, preferably chlorine, can occur also more than once, in particular twice, or in addition to one of the substituents mentioned hereinabove. Throughout the specification the term lower is to be understood as meaning that the group in question contains not more than 7, and preferably not more than 4 carbon atoms.

The basically substituted pyridinecarboxamides of the present invention possess advantageous pharmacological properties. Thus they antagonise the emetic effect of apomorphine in dogs when administered in doses from approx. 0.05 mg/kg per os or subcutaneously, and they also antagonise amphetamine stereotypy and apomorphine stereotypy in rats when administered in doses from approx. 5 mg/kg per os. The antagonistic effect on amphetamine stereotypy was determined according to the method described by J. Del Rio and J. A. Fuentes, Eur. J. Pharmac. 8, 73–78 (1969); but only the inhibition of the lick reaction was employed as yardstick for evaluating the antagonistic effect. The antagonistic effect on the stereotyped behaviour induced by apomorphine was determined according to the method of P. A. J. Janssen, C. J. E. Niemgeers, K. A. L. Schellekens and F. Lenaerts, Arzneimittel-Forsch. 17, 841 (1966). This method was modified to the extent that only the inhibition of chewing induced by apomorphine served as yardstick for determining the antagonistic effect. In addition, when administered to rats in doses from approx. 25 mg/kg p.o. the basically substituted pyridinecarboxamides of the general formula I increase the endogenic content of homovallinic acid and of 3,4-dihydroxyphenylacetic acid in the corpus striatum of the rats - a fact which points to an increase in the dopamine turnover, cf. G. F. Murphy et al., Brit. J. Pharmacol. 36, 107–115 (1969), N. E. Anden et al., Life Sci. 2, 448–458 (1963), D. F. Sharman in Methods of Neurochemistry, R. Fried ed., p. 111; New York: Dekker 1971. The basically substituted pyridinecarboxamides of the general formula I are also characterised by a rapid onset of action and can be used as antiemetics, psychosomatics and antipsychotics, for example for treating thought disturbances which manifest themselves e.g. in delusions, and psychomoter excitation of different origin.

The present invention provides in particular pyridinecarboxamides of the general formula I, wherein $R_1$ represents lower alkyl, particularly methyl, $R_2$ represents lower alkyl, particularly ethyl, and A represents trimethylene $m$ and $n$ are as defined in formula I but preferably $m$ is 0 and $n$ is 1, and the ring B is substituted only by $O-R_1$ or in addition by halogen with an atomic number up to 35, particularly chlorine, by lower alkyl, for example methyl, lower alkoxy, for example methoxy or ethoxy, lower alkylthio, for example methylthio or ethylthio, lower alkylsulphinyl or lower alkylsulphonyl, for example methylsulphinyl, ethylsulphinyl or methylsulphonyl or ethylsulphonyl, or also by di-lower alkylamino, for example dimethylamino, or by cyano, and the acid addition salts thereof, in particularly the pharmaceutically acceptable acid addition salts.

Primarily the invention provides pyridinecarboxamides of the general formula I, wherein $R_1$ represents methyl, $R_2$ represents lower alkyl, preferably ethyl, A represents trimethylene, m is 0 and n is 1, and the ring B is substituted only by O—$R_1$ or is preferably further disubstituted and chiefly monosubstituted by chlorine, methyl or methoxy, in particular corresponding picolinamides and principally nicotinamides, such as N-[(1-ethyl-2-pyrrolidinyl)-methyl]-3-methoxypicolinamide, N-[(1-ethyl-2-pyrrolidinyl)-methyl]-3-methoxy-6-methylpicolinamide, N-[(1-ethyl-2-pyrrolidinyl)-methyl]-4-methoxynicotinamide, N-[(1-ethyl-2-pyrrolidinyl)-methyl]-2-methoxy-6-chloronicotinamide and particularly N-[(1-ethyl-2-pyrrolidinyl)-methyl]-2,6-dimethoxynicotinamide, and the pharmaceutically acceptable acid addition salts thereof, for example the hydrochlorides.

The compounds of the general formula I are obtained according to the invention by (a) reacting a pyridinecarboxylic acid of the general formula II

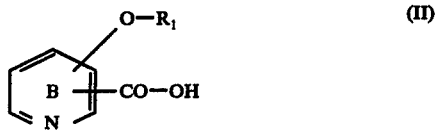

(II)

wherein $R_1$ represents lower alkyl, O—$R_1$ is in the adjacent position to the carboxyl group, and the ring B can be further substituted if desired, or a reactive functional derivative thereof, with a compound of the general formula III

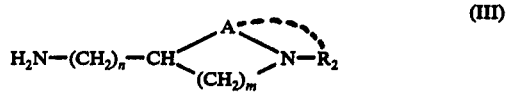

(III)

wherein $R_2$, A, m and n are as defined in formula I, or with a reactive functional derivative thereof, or (b) reacting a compound of the general formula IV

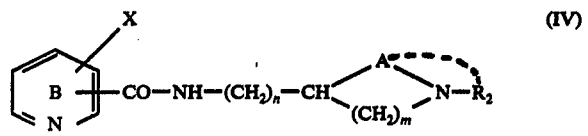

(IV)

wherein X is always in the adjacent position to the carboxamide group and represents halogen from atomic number 17 or hydroxy, and $R_2$, A, m and n are as defined in formula I and the ring B can be further substituted if desired, if X is halogen, with a metal compound of a lower alkanol, or, if X is hydroxy, etherifying it by a lower alkyl group, and, if desired, reducing the compound obtained, provided it contains chlorine or bromine as substituent of the ring B, to give the corresponding compound with hydrogen in the corresponding position, or reacting it with a metal compound of a lower alkanol or lower alkane thiol and/or, if desired, converting a resultant compound of the general formula I into an acid addition salt.

Process (a) is carried out by reacting for example a pyridinecarboxylic acid of the general formula II with a compound of the general formula III, in the presence of a dehydrating condensation agent, for exaple a N,N'-disubstituted carbodiimide, such as N,N'-dicyclohexylcarbodiimide, a derivative of trivalent or pentavalent phosphorus, for example triphenylphosphite, tetraethylpyrophosphite, 4-methyl-2-chloro-1,3,2-dioxaphosphorinane or phosphorus pentoxide, or of a halosilane, such as tetrachlorosilane or trichlorophenylsilane, for example in an inert organic solvent, for example dioxane or tetrahydrofurane, at room temperature or elevated temperature, preferably at the boiling temperature of the solvent, or, especially when using phosphorus pentoxide, also in the absence of solvents at temperatures of up to approx. 160° C.

Suitable reactive functional derivatives of pyridinecarboxylic acids of the general formula II are for example the lower alkyl esters thereof, such as the ethyl esters and, in particular, the methyl esters, which, on being heated with compounds of the general formula III preferably to at least the boiling temperature of the corresponding lower alkanol and to at most 180° C, in the presence or absence of an inert organic solvent, for example toluene or xylene and/or an excess of the compound of the general formula III, yield substituted pyridinecarboxamides of the general formula I. Under essentially the same or somewhat milder reaction conditions, it is possible to react activated esters, for example the cyanomethyl esters obtained by reacting pyridinecarboxylic acids of the general formula I with chloroacetonitrile in the presence of acid acceptors, or the p-nitrophenyl esters with compounds of the general formula III. Examples of further suitable reactive functional derivatives of pyridinecarboxylic acids of the formula I are the anhydrides thereof, especially mixed anhydrides, such as halides, in particular chlorides, and anhydrides with carbonic acid hemiesters, such as the anhydrides with lower alkoxy formic acids obtained, for example, from the carboxylic acids by reaction with lower alkyl esters of chloroformic acid in the presence of bases. These functional derivatives are reacted with a compound of the general formula III, preferably in the presence of an acid acceptor, for example a strong tertiary organic base, such as triethylamine, N-ethyldiisopropylamine, pyridine or s-collidine, an excess of which can also be used as reaction medium, or of an excess of the reaction component of the general formula III, in the presence or absence of an inert organic solvent, for example dioxane, tetrahydrofurane, methylene chloride, chloroform, benzene or dimethyl formamide. Examples of further suitable derivatives of the carboxylic acids of the general formula II are the 1-imidazolides obtained by reacting the carboxylic acids with 1,1'-carbonyldiimidazole or with 1,1'-sulphonyldiimidazole, and the isothiocyanates thereof, which are reacted with compounds of the general formula III preferably in inert organic solvents, for example tetrahydrofurane, dioxane or ethyl methyl ketone, if necessary with heating.

Further suitable reaction functional derivatives of pyridinecarboxylic acids of the general formula II are also certain enol esters, in particular the enol esters of N-ethyl-3-oxo-3-(m-sulphobenzoyl)-propionamide obtained by reacting the pyridinecarboxylic acids with N-ethyl-5-phenylisooxazolium-3'-sulphonate [cf. R. B. Woodward et al., J. Am. Chem. Soc. 83, 1010 (1961)].

Examples of suitable reactive functional derivatives of compounds of the general formula III are corresponding isocyanates and isothiocyanates (cf. German Offenlegungsschrift No. 2,327,414) and phosphoric triamides (cf. German Offenlegungsschrift No. 2,162,917) which can be reacted with pyridinecarboxylic acids of the general formula II in inert organic solvents, for example dioxane, benzene, toluene or xylenes, at elevated temperatures up to approx. 150° C or at the boiling temperature of the solvent. Mention may also be made of the reaction products of phosphorus trichloride and twice the molar amount of a compound of the general formula III (cf. German Offenlegungsschrift No. 2,327,193), which are formed in pyridine and are preferably reacted in situ at boiling temperature with pyridinecarboxylic acids of the general formula II, and N-sulphenyl derivatives of compounds of the general formula III, such as the N-(2-pyridinesulphenyl) derivatives (cf. German Offenlegungsschrift No. 2,452,405), which are formed preferably from the compounds of the general formula III with organic disulphides, such as di-(2-pyridyl)sulphide, in an inert organic solvent, such as dimethyl formamide, dioxane, methylene chloride, benzene or pyridine, and are reacted in situ in the presence of compounds of trivalent phosphorus, such as triphenylphosphine, at room temperature, with pyridinecarboxylic acids of the general formula II.

As further reactive functional derivatives of compounds of the general formula III mention is also to be made of the N-trimethylsilyl derivatives which can be obtained by reacting these amines with trimethylsilyl chloride in inert anhydrous organic solvents and which react with reactive functional derivatives of acids of the general formula II in inert organic solvents to give N-trimethylsilyl derivatives of compounds of the general formula I, from which the desired amides are obtained by decomposition with water or lower alkanols.

The reaction of a compound of the general formula IV, in which a halogen atom X is preferably in 2- or 4-position, with a metal compound of a lower alkanol, in particular with an alkali metal lower alkoxide, such as sodium or potassium ethoxide or especially methoxide, is preferably carried out in the corresponding lower alkanol at temperatures between approx. 0° and 100° C or the boiling temperature of the lower alkanol respectively. However, it is also possible to use as solvent another inert organic solvent, for example dimethyl formamide, dimethyl sulphoxide, N,N,N',N',N'',N''-hexamethylphosphoric triamide, tetrahydrofurane, dioxane, benzene or toluene.

The etherification of a hydroxy group X, which is preferably in the 3-position of a starting material of the general formula IV, can be carried out in known manner. Thus the starting material can be reacted for example with a diazo lower alkane, for example diazomethane, diazoethane or diazo-n-butane. Such a reagent is employed in the presence of a suitable inert solvent, such as an aliphatic or aromatic hydrocarbon which can be substituted for example by halogen, such as chlorine, or of a solvent mixture, and, depending on the diazo reagent, with cooling, at room temperature or with gentle heating, and, if necessary, in a closed vessel and/or in an inert gas atmosphere, for example in an atmosphere of nitrogen.

It is also possible to convert a starting material of the general formula IV by treatment with a reactive ester of a lower alkanol into a compound of the general formula I. Suitable esters are chiefly those with strong inorganic or organic acids, such as mineral acids, for example hydrohalic acids, for example hydrochloric, hydrobromic or hydroiodic acid, and sulphuric or halosulphuric acids, for example fluorosulphuric acid, or strong organic sulphonic acids, such as lower alkanesulphonic acids which can be substituted for example by halogen, for example fluorine, or aromatic sulphonic acids, for example benzenesulphonic acids which can be substituted for example by lower alkyl, such as methyl, halogen, such as bromine, and/or nitro, for example methanesulphonic, trifluoromethanesulphonic or p-toluenesulphonic acid. These reagents, in particular di-lower alkyl sulphates, such as dimethyl sulphate, and lower alkyl fluorosulphates, for example methyl fluorosulphate, or lower alkyl esters of unsubstituted or halogen-substituted methanesulphonic acid, for example trifluoromethane methylsulphonate, are ordinarily used in the presence of a solvent, for example an aliphatic, cycloaliphatic or aromatic hydrocarbon which can be substituted for example by halogen, such as chlorine, for example methylene chloride, of an ether, such as dioxane or tetrahydrofurane, or of a lower alkanol, such as methanol, or of a solvent mixture. In addition, it is preferred to use suitable condensation agents, for example alkali metal lower alkoxides, such as sodium methoxide, and alkali metal carbonates or alkali metal hydrogen carbonates, for example sodium or potassium carbonate or sodium or potassium hydrogen carbonate (usually together with a sulphate), or in aprotic solvents, for example also alkali metal hydrides, such as sodium hydride, or organic bases, for example preferably sterically hindered tri-lower alkylamines, for example N,N-diisopropyl-N-ethylamine, as a rule together with lower alkyl halogen sulphates or lower alkyl esters of unsubstituted or halogen-substituted methanesulphonic acid, the process being carried out with cooling, at room temperature or with heating, for example at temperatures of approx. $-20°$ to approx. $+50°$ C, and, if necessary, in a closed vessel and/or in an inert gas atmosphere, for example in an atmosphere of nitrogen.

The conversion of a starting material of the general formula IV with a hydroxyl group, preferably in 3-position, into a compound of the general formula I can also be carried out by treatment with a compound which contains two or three lower alkoxy groups at the same carbon atom of aliphatic character, i.e. with a corresponding acetal or ortho-ester, in the presence of an acid agent. Thus, for example, gem-lower alkoxy-lower alkanes, such as 2,2-dimethoxypropane, can be used as etherifying agents in the presence of a strong organic sulphonic acid, such as p-toluenesulphonic acid, and a suitable solvent, such as a lower alkanol, for example methanol, or of a di-lower alkyl sulphoxide or a lower alkylene sulphoxide, for example dimethyl sulphoxide, or tri-lower alkyl esters of orthoformic acid, for example triethyl orthoformate, can be used in the presence of a strong acid, such as a mineral acid, for example sulphuric acid, or of a strong organic sulphonic acid such as p-toluenesulphonic acid, and of a suitable solvent, such as a lower alkanol, for example ethanol, or of an ether, for example dioxane.

Compounds of the general formula I can also be obtained by reacting starting materials of the general formula IV, in which X represents a hydroxy group, with tri-lower alkyl oxonium salts, and with di-lower alkoxy carbenium salts or di-lower alkyl halonium salts, wherein halonium is in particular bromonium, especially with corresponding salts with complex, fluorine-containing acids, such as the corresponding tetrafluoroborates, hexafluoroborates, hexafluoroantimonates or hexachloroantimonates. Such reagents are, for example, trimethyloxonium- or triethyloxonium-hexafluoroantimonate, -hexachloroantimonate, -hexafluorophosphate or -tetrafluoroborate, dimethoxycarbeniumhexafluorophosphate or dimethylbromoniumhexafluoroantimonate. These etherifying agents are preferably used in an inert solvent, such as an ether or a halogenated hydrocarbon, for example diethyl ether, tetrahydrofurane or methylene chloride, or in a mixture thereof, if necessary in the presence of a base, such as an organic base, for example a preferably sterically hindered tri-lower alkyl-amine, for example N,N-diisopropyl-N-ethylamine, and with cooling, at room temperature or with gentle heating, for example at approx. −20° to approx. +50° C, if necessary in a closed vessel and/or in an inert gas atmosphere, for example in an atmosphere of nitrogen.

The etherification of the hydroxyl group in a starting material of the general formula IV can also be effected by treatment with a 3-substituted 1-lower alkyl triazine compound, wherein the substituent of the 3-nitrogen atom represents an organic radical which is bound through a carbon atom, preferably a carbocyclic aryl radical, such as a substituted or unsubstituted phenyl radical, for example lower alkylphenyl, such as 4-methyl-phenyl. Such triazene compounds are 3-aryl-1-lower alkyl-triazenes, for example 3-(4-methylphenyl)-1-methyl-triazene. These reagents are normally used in the presence of inert solvents, such as optionally halogenated hydrocarbons or ethers, for example benzene, or solvent mixtures, and with cooling, at room temperature and preferably at elevated temperature, for example at approx. 20° to approx. 100° C, if necessary in a closed vessel and/or in an inert gas atmosphere, for example in an atmosphere of nitrogen.

The reaction of pyridinecarboxamides of the general formula I which contain a halogen atom in the ring B, in particular a chlorine or bromine atom, with metal compounds of lower alkanols or lower alkane thiols, is carried out in accordance with process (b) above and, if appropriate, in the same operation as this process, i.e. if desired a compound of the general formula IV, which, in addition to the halogen atom X contains a second reactive halogen atom as substituent of the ring B, can also be reacted directly with twice the molar amount of a metal compound of a lower alkanol.

The reduction of pyridinecarboxamides of the general formula I which contain a halogen atom in the ring B in order to replace this halogen atom with hydrogen can be carried out for example in conventional manner with hydrogen in the presence of a hydrogenation catalyst, for example a noble metal catalyst, such as palladium on carbon, or of a heavy metal catalyst, such as Raney nickel, in an inert organic solvent, such as methanol, ethanol, dioxane or tetrahydrofurane, at room temperature and normal pressure or moderately elevated temperatures and/or pressures.

A number of representatives of the pyridinecarboxylic acids of the general formula II and their reactive functional derivatives and also of the compounds of the general formula III and their reactive functional derivatives are known and others can be obtained in a manner analogous to that of the known compounds. Pyridinecarboxylic acids of the general formula II and suitable derivatives, such as the lower alkyl esters, in which the ring B is substituted by lower alkylsulphinyl or lower alkylsulphonyl, are obtained preferably by oxidising the corresponding lower alkylthiosubstituted compounds, for example with m-chloroperoxybenzoic acid in an inert organic solvent, for example methylene chloride or chloroform. The starting materials of the general formula IV can be obtained in a manner analogous to that employed to obtain the compounds of the general formula I, i.e. analogous to process (a), from pyridinecarboxylic acids which are partly known and substituted by X and optionally additionally substituted, or their reactive functional derivatives, and compounds of the general formula III or their reactive functional derivatives.

The present invention also relates to those modifications of the processes described in (a) and (b) and their primary steps, in which a process is discontinued at any stage or in which a compound occurring in any stage as intermediate is used as starting material and the missing steps are carried out, or in which a starting material is formed under the reaction conditions or, if appropriate, is used in the form of a salt.

If the required starting materials are optionally active – which always applies to the compounds of the general formula III – it is possible to use both the racemates and the isolated antipodes, or, if diastereomism occurs, either racemic mixtures or specific racemates or also isolated antipodes. Such starting materials can also be used, if appropriate, in the form of salts.

Preferably those starting material which result in the groups of end products particularly referred to at the outset are used for carrying out the reactions of the present invention.

Depending on the process conditions and starting materials, the starting materials are obtained in the free form or in the form of their acid addition salts, which are also comprised by the invention, or, if appropriate, also as hydrates of these latter. The acid addition salts of the novel compounds of the general formula I can be converted in known manner into the free bases, for example with basic agents, such as alkalies or ion exchangers. On the other hand, the compounds of the general formula I obtained by the processes of this invention can be converted, if desired, in conventional manner into their addition salts with inorganic or organic acids. For example, a solution of a compound of the general formula I is treated in an organic solvent with the acid desired as salt component. Preferably organic solvents in which the resultant salt is sparingly soluble is chosen for the reaction, so that it can be separated by filtration. Examples of such solvents are: ethyl acetate, methanol, ethers, acetone, methyl ethyl ketone, acetone-ether, acetone-ethanol, methanol-ether or ethanol-ether.

Instead of using free bases, it is possible to use pharmaceutically acceptable acid addition salts as medicinal substances, i.e. salts with those acids whose anions are non-toxic in the intended doses. It is also advantageous if the salts to be used as medicinal substances are readily crystallisable and are not hygroscopic or are hygroscopic to an insignificant degree. The following acids for example can be used for the salt formation with compounds of the general formula I: hydrochloric acid, hydrobromic acid, sulphuric acid, phosphoric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicyclic acid, phenylacetic acid, mandelic acid and embonic acid.

Depending on the choice of starting materials and methods of operation, the compounds of the present invention can be obtained as optical antipodes or racemates, or, if they contain two asymmetrical carbon atoms, can also be in the form of isomeric mixtures (racemic mixtures). Isomeric (racemic) mixtures can be separated in known manner into the two stereoisomeric (diastereomeric) pure racemates on the basis of the physicochemical differences of the constituents, for example by chromatography and/or fractional crystallisation.

Resultant racemates can be separated by known methods into their optical antipodes, for example by recrystallisation from an optically active solvent, with the aid of microorganisms or by reaction with an optically active acid which forms salts with the racemic compound and separating the salts so obtained, for example on the basis of their different solubilities, into the diastereoisomers, from which the antipodes can be liberated by treatment with suitable agents. Particularly common optically active acids are for example the D- and L-forms of tartaric acid, di-ortho-toluoyl-tartaric acid, malic acid, mandelic acid, camphorsulphonic acid or quinic acid.

The active ingredients of this invention are administered perorally, rectally or parenterally. The dosage depends on the mode of application, the species, the age, and the individual condition. The daily doses of the free bases or of pharmaceutically acceptable salts thereof are in the range between 1 mg/kg and 25 mg/kg for warm-blooded animals. Suitable dosage forms, such as coated tablets, tablets, suppositories or ampoules, contain preferably 10 to 100 mg of an active ingredient of the invention.

Dosage forms for peroral administration contain as active ingredient preferably between 0.5 and 50% of a compound of the general formula I or of a pharmaceutically acceptable salt thereof. They are prepared by combining the active ingredient for example with solid, powdery carriers, such as lactose, saccharose, sorbitol, mannitol; starches, such as potato starch, corn starch or amylopectin, laminaria powder or citrus pulp powder; cellulose derivatives or gelatin, with or without the addition of lubricants, such as magnesium or calcium stearate or polyethylene glycols, to give tablets or coated tablet cores. The coated tablet cores are coated for example with concentrated sugar solutions, which can additionally contain gum arabic, talcum and/or titanium dioxide, or with a lacquer which is dissolved in readily volatile organic solvents or solvent mixtures. Colourants can be added to these coatings, for example to distinguish different dosages of active ingredient.

Further suitable oral dosage forms are hard gelatin capsules and soft gelatin capsules which are plasticised with glycerol. The hard gelatin capsules preferably contain the active ingredient in granulate form, for example in admixture with fillers, such as corn starch, and/or lubricants, such as talc or magnesium stearate, and optionally stabilisers, such as sodium meta-bisulphite (Na$_2$S$_2$O$_5$) or ascorbic acid. In soft gelatin capsules the active ingredient is preferably dissolved or suspended in suitable liquids, such as liquid polyethylene glycols, to which stabilisers can also be added.

Suitable dosage forms for rectal administration are for example suppositories, which consist of a combination of an active ingredient with a suppository base. Examples of suitable suppository bases are natural or synthetic triglycerides, paraffin hydrocarbons, polyethylene glycols or higher alcohols. Gelatin rectal capsules, which consist of a combination of the active ingredient with a base material are also suitable. Suitable base materials are for example liquid triglycerides, polyethylene glycols or paraffin hydrocarbons.

Ampoules for parenteral, in particular intramuscular, administration contain preferably a water-soluble salt of an active ingredient in a concentration of preferably 0.2 to 5%, optionally together with suitable stabilisers and buffer substances, in aqueous solution.

The following directions will serve to illustrate the preparation of tablets, sugar coated tablets, suppositories and ampoules in more detail without restricting the scope of the invention:

(a) 500 g of N-[(1-ethyl-2-pyrrolidinyl)-methyl]-3-methoxypicolinamide hydrochloride are mixed with 500 g of lactose and 292 g of potato starch. The mixture is moistened with an alcoholic solution of 8 g of gelatin and granulated through a sieve. After the moist granulate has dried, it is mixed with 60 g of potato starch, 60 g of talc, 10 g of magnesium stearate and 20 g of highly disperse silica, and the mixture is pressed to 10,000 tablets each weighing 145 mg and containing 50 mg of active ingredient. If desired, the tablets can be provided with a breaking notch for finer adjustment of the dosage.

(b) 25 g of N-[(1-ethyl-2-pyrrolidinyl)-methyl]-2,6-dimethoxynicotinamide hydrochloride are thoroughly mixed with 16 g of corn starch and 6 g of highly disperse silica. The mixture is moistened with a solution of 2 g of stearic acid, 6 g of ethyl cellulose and 6 g of stearin in approx. 70 ml of isopropyl alcohol and granulated through a sieve of 1.2 mm mesh width. The granulate is dried for approx. 14 hours and then forced through a sieve of 1.2–1.5 mm mesh width. Thereafter it is mixed with 16 g of corn starch, 16 g of talc and 2 g of magnesium stearate and pressed to 1000 coated tablet cores. These cores are coated with a concentrated syrup of 2 g of lacca, 7.5 g of gum arabic, 0.15 g of dye, 2 g of highly disperse silica, 25 g of talc and 53.35 g of sugar, and dried. Each of the sugar coated tablets weighs 185 g and contains 25 mg of active ingredient.

(c) 100 g of N-[(1-ethyl-2-pyrrolidinyl)-methyl]-2,6-dimethoxynicotinamide and 1900 g of finely ground suppository base (e.g. cocoa butter) are thoroughly mixed and the mixture is then melted. From the melt, which is kept homogeneous by stirring, 1000 suppositories each weighing 2 g are cast. Each suppository contains 100 mg of active ingredient.

(d) 1000 ampoules are filled with a solution of 10 g of N-[(1-ethyl-2-pyrrolidinyl)-methyl]-3-methoxy-6-methylpicolinamide and hydrochloric acid to a pH of 7.4 in one liter of water, and sterilised. Each ampoule contains 10 mg of active ingredient as 1% solution. It is also possible to use 10 g of N-[(1-ethyl-2pyrrolidinyl)-methyl]-4-methoxynicotinamide as active ingredient.

The following Examples illustrate the preparation of the novel compounds of the general formula I and of hitherto unknown starting materials, but do not in any way restrict the scope of the invention.

EXAMPLE 1

6.7 g (0.04 mole) of methyl 4-methoxynicotinate (m.p. 82°–83° C, W. C. J. Ross, J. Chem. Soc. 1966, 1816) and 7.18 g (0.06 mole) of 1-ethyl-2-(aminomethyl)-pyrrolidine are dissolved in 50 ml of xylene and the solution is heated for 6 hours so that a slow distillation takes place. Approx. 15 ml of distillate with a boiling point of 60°–80° C are collected. The mixture is then completely concentrated in a high vacuum at 50°–60° C and the oily residue obtained is chromatographed through a column of 200 g of basic silica gel. Pure N-[(1-ethyl-2-pyrrolidinyl)-methyl]-4-methoxynicotinamide is obtained as an oil with benzene-methanol (99:1) as eluant.

Thin-layer chromatogram: (silica gel) in the system acetone-ethyl acetate-concentrated ammonia = 50:50:6; $R_f = 0.65$.

EXAMPLE 2

10.5 g (0.063 mole) of methyl 3-methoxypicolinate and 17.6 g (0.137 mole) of 1-ethyl-2-(aminomethyl)-pyrrolidine are heated under nitrogen for 6 hours to 80° C. The excess base is distilled off in a high vacuum at 50° C and the oily residue is dissolved in methylene chloride and treated with 12 ml of 6 N ethanolic hydrochloric acid. The solvent is evaporated in vacuo and the oily residue is crystallised by trituration with ether. The crystals are collected by filtration and recrystallised from isopropanol-ethyl acetate to yield crude N-[(1-ethyl-2-pyrrolidinyl)-methyl]-3-methoxypicolinamide hydrochloride. The combined mother solutions are concentrated in vacuo and the free base is recovered as solution with 2 N sodium hydroxide solution and methylene chloride. The solution is concentrated, the residue dissolved in chloroform and chromatographed through a column of 60 g of silica gel with chloroform-methanol (98:2) as eluant. The base so obtained is again converted with ethanolic hydrochloric acid into the hydrochloride, which is recrystallised from ether. The combined crude hydrochlorides are recrystallised from isopropanol-ethyl acetate and yield pure N-[(1-ethyl-2-pyrrolidinyl)-methyl]-3-methoxypicolinamide hydrochloride with a melting point of 162°–163° C.

EXAMPLE 3

By carrying out the procedure described in Example 1, pure N-[(1-ethyl-2-pyrrolidinyl)-methyl]-3-methoxy-6-methylpicolinamide is obtained as an oil, after analogous chromatography, from 3.62 g (0.02 mole) of methyl 3-methoxy-6-methylpicolinate and 3.59 g (0.03 mole) of 1-ethyl-2-(aminomethyl)-pyrrolidine. Thin-layer chromatogram: (silica gel) in the system acetone-ethyl acetate-concentrated ammonia = 70:30:6; $R_f = 0.45$-$0.50$.

Methyl 3-methoxy-6-methylpicolinate is obtained as follows:

(a) While cooling with ice-water, 30.6 g (0.2 mole) of 3-hydroxy-6-methylpicolinic acid (cf. T. Urbanski, J. Chem. Soc. 1947, 132-134) are added slowly to a suspension of 11.5 g (0.48 mole) of sodium hydride in 200 ml of hexamethylphosphoric triamide. The mixture is thereafter heated to 70° C in the course of 40 minutes and stirred for 30 minutes at this temperature. After the batch has cooled to 35°–40° C, a solution of 59 g (0.42 mole) of methyl iodide in 50 ml of benzene is added dropwise in the course of 2 hours. After completion of addition, the mixture is heated for 5 hours to 70° C and poured onto a mixture of ice and water. The aqueous solution is adjusted to a pH of 7 with a small amount of 2 N hydrochloric acid and phosphate buffer, saturated with sodium chloride and extracted with six 400 ml portions of ethyl acetate. The ethyl acetate extracts are dried over magnesium sulfate and evaporated to dryness. The residue is crystallised from ether-pentane to yield pure methyl 3-methoxy-6-methylpicolinate with a melting point of 55°–57° C.

EXAMPLE 4

19.7 g (0.1 mole) of methyl 2,6-dimethoxynicotinate and 64 g (0.5 mole) of 1-ethyl-2-(aminomethyl)-pyrrolidine are heated for 6 hours to 90° C. The excess base is then distilled off from the reaction mixture in a water jet vacuum at 50° to 60° C and the residue is dried in a high vacuum. The crude product is chromatographed through a column of 250 g of basic silica gel with benzene which contains 0.5% of methanol. Crystallisation of the homogeneous fractions from pentane yields N-[(1-ethyl-2-(pyrrolidinyl)-methyl]-2,6-dimethoxynicotinamide with a melting point of 76°–77° C.

The methyl 2,6-dimethoxynicotinate required as starting material is obtained as follows:

(a) 19.1 g (0.1 mole) of 2,6-dichloronicotinic acid [Guthzeit and Laska, J. pr. Ch. 58 [2], 425 (1898)] are suspended in 250 ml of methanol and, while stirring and cooling with ice, hydrogen chloride gas is introduced until the mixture is saturated. The reaction mixture is allowed to stand for 48 hours at room temperature and subsequently heated for 3 hours to reflux temperature. It is then evaporated to dryness in a high vacuum at 40° C and the residue is dried in a high vacuum at 40° C. The brown crystalline product is recrystallised from ether-pentane to yield methyl 2,6-dichloronicotinate with a melting point of 53°–54° C.

(b) 31 g (0.15 mole) of methyl 2,6-dichloronicotinate are dissolved in 100 ml of methanol and a solution of 6.90 g (0.30 mole) of sodium in 150 ml of absolute methanol is added dropwise at 20°–40° C in the course of 15 minutes. The reaction mixture is subsequently refluxed for 3 hours, then evaporated to dryness in vacuo and the residue is taken up in benzene. The benzene solution is filtered to remove undissolved matter, concentrated in vacuo, and the resultant crystalline substance is distilled in a high vacuum (b.p. 85°–95° C/0.001 Torr). The crystalline distillate is recrystallised from petroleum ether-pentane to yield pure methyl 2,6-dimethoxynicotinate with a melting point of 52°–54° C.

EXAMPLE 5

8.35 g (0.050 mole) of methyl 3-methoxyisonicotinate [obtained according to the method of L. Novacek, U. Palet, M. Celadnik and E. Matuskova, Ceskoslav. Farm. 11, 76–79 (1962); C.A. 57, 15067 h (1962)] and 13.3 g (0.104 mole) of 1-ethyl-2-(aminomethyl)-pyrrolidine are heated, with stirring, for 6 hours to 80° C. Excess 1-ethyl-2-(aminomethyl)-pyrrolidine is then distilled off in a vacuum of 0.10 Torr. The residue is dissolved in acetone and ethereal hydrogen chloride solution is added thereto until the onset of a weak acid reaction to Congo red. N-[(1-ethyl-2-pyrrolidinyl)-methyl]-3-methoxyisonicotinamide hydrochloride is then precipitated by addition of ether. It melts at 132°–135° C after 3 recrystallisations from acetone-ether.

EXAMPLE 6

5.02 g (0.025 mole) of crude 2-methoxy-6-chloronicotinoyl chloride are dissolved in 75 ml of absolute chloroform and the solution is added dropwise in the course of 30 minutes at 25°–30° C to a solution of 7.7 g (0.06 mole) of 1-ethyl-2-(aminomethyl)-pyrrolidine in 75 ml of absolute benzene. The reaction mixture is stirred for 3 hours at 50° C, cooled, and 10 ml of a 5 N ethanolic ammonia solution are added thereto. The organic solvents are evaporated in vacuo and the residual crude base is chromatographed through a column of basic silica gel with benzene which contains 0.5% of methanol. Pure N-[(1-ethyl-2-pyrrolidinyl)-methyl]-2-methoxy-6-chloronicotinamide is obtained as an oil.

The 2-methoxy-6-chloronicotinoyl chloride is obtained as follows:

(a) A sodium methoxide solution prepared from 3.46 g (0.15 mole) of sodium and 150 ml of absolute methanol is added dropwise at 40° C in the course of 1 hour to a solution of 312 g (0.15 mole) of methyl 2,6-dichloronicotinate in 100 ml of methanol. The reaction mixture is refluxed for 3 hours and the solvent is then evaporated in vacuo. The dry residue is triturated with methylene chloride, the undissolved constituents are filtered off and the filtrate is evaporated in vacuo to dryness. The crystallised residue is recrystallised from petroleum ether to yield pure methyl 2-methoxy-6-chloronicotinate with a melting point of 68°–69° C.

(b) A solution of 10.1 g (0.05 mole) of methyl 2-methoxy-6-chloronicotinate in 20 ml of methanol is added dropwise at 70° C in the course of 30 minutes to 500 ml of 0.1 N aqueous sodium hydroxide solution. After completion of the addition, the mixture is refluxed for 1 hour. The clear solution is concentrated in vacuo to approx. 100 ml and acidified with 2 N hydrochloric acid to pH 3. The precipitate which has formed is collected by filtration, washed with a small amount of water and dried. The residue is recrystallized from benzene-petroleum ether to yield pure 2-methoxy-6-chloronicotinic acid with a melting point of 210°–215° C.

(c) 3.7 g (0.08 mole) of 2-methoxy-6-chloronicotinic acid are suspended in 60 ml of thionyl chloride and the suspension is heated for 3 hours to 60° C. The reaction mixture is evaporated to dryness in vacuo, dissolved in three 50 ml portions of benzene and evaporated to dryness again each time. The residual crude, partly crystallised 2-methoxy-6-chloronicotinoyl chloride is dried for 2 hours in a high vacuum and further used without purification.

EXAMPLE 7

10.5 g (0.33 mole) of N-[(1-ethyl-2-pyrrolidinyl)-methyl]-2,6-dichloronicotinamide are dissolved in 50 ml of absolute methanol and to this solution is added dropwise a sodium methoxide solution prepared from 0.75 g (0.33 mole) of sodium and 100 ml of absolute methanol in the course of 90 minutes at 40°–45° C. The reaction mixture is kept for 1 hour at 40°–45° C and the methanol is thereafter evaporated in vacuo to a volume of 50 ml. The concentrate is poured onto ice-water, saturated with potassium carbonate and extracted twice with benzene. The organic phases are dried over magnesium sulphate and the solvent is then evaporated in vacuo. The oily residue is chromatographed through a column of basic silica gel with benzene to which 0.5% of methanol is added. Pure N-[1-ethyl-2-pyrrolidinyl)-methyl]-2-methoxy-6-chloronicotinamide is obtained as an oil.

The dichloro compound is obtained as follows:

(a) 10.1 g (0.1 mole) of 2,6-dichloronicotinic acid are suspended in 100 ml of thionyl chloride and, with the addition of 0.1 ml of dimethyl formamide, the suspension is heated for 3 hours to 45°–50° C. The resultant clear solution is evaporated to dryness in vacuo and the residue is dissolved in three 100 ml portions of benzene and on each occasion the solution is subsequently evaporated to dryness. The residue consisting of oily, partly crystallised 2,6-dichloronicotinoyl chloride is dried in a high vacuum and further used without purification.

(b) The above acid chloride is dissolved in 150 ml of absolute chloroform and the solution is added dropwise in the course of 30 minutes at 23°–30° C to a solution of 15.4 g (0.12 mole) of 1-ethyl-2-(aminomethyl)-pyrrolidine in 150 ml of absolute benzene. The reaction mixture is stirred for 3 hours at 50° C, cooled, and 20 ml of a 5 N ethanolic ammonia solution is added thereto. The organic solvents are evaporated in vacuo and the residue is extracted with benzene and filtered. The benzene solution is again concentrated and the residual crude base is chromatographed through a column of basic silica gel with benzene to which 0.5% of methanol has been added, to yield pure N-[(1-ethyl-2-pyrrolidinyl)-methyl]-2,6-dichloronicotinamide with a melting point of 73°–74° C.

EXAMPLE 8

9.07 g (0.030 mole) of N-[(1-ethyl-2-pyrrolidinyl)-methyl]-2,6-dichloronicotinamide [cf. Example 7 b)] are dissolved in 50 ml of methanol and the solution is treated with a sodium methoxide solution prepared from 1.52 g (0.066 mole) of sodium in 100 ml of absolute methanol. The reaction mixture is heated for 3 hours to 60° C and subsequently concentrated in vacuo to 50 ml. The concentrate is poured onto ice-water, saturated with potassium carbonate and extracted with benzene. The benzene solutions are dried over magnesium sulphate and the solvent is evaporated in vacuo. The oily residue is chromatographed through a column of basic silica gel with benzene to which 0.5% of methanol is added. The pure N-[(1-ethyl-2-pyrrolidinyl)-methyl]-2,6-dimethoxynicotinamide melts at 76°–77° C.

N-[(1-ethyl-2-pyrrolidinyl)-methyl]-2,6-dimethoxy-5-chloronicotinamide, with a melting point of 94°–95° C, is obtained in analogous manner using 10.1 g (0.030 mole) of N-[(1-ethyl-2-pyrrolidinyl)-methyl]-2,5,6-trichloronicotinamide (crude product, see below) and a sodium methoxide solution prepared from 1.38 g (0.060 mole) of sodium in 100 ml of absolute methanol.

The starting material is prepared from 32 g (0.1 mole) of 2,5,6-trichloronicotinic acid [cf. F. Mutterer and C. D. Weis, Helv. Chim. Acta 59, 222 (1976)] by conversion into the 2,5,6-trichloronicotinoyl chloride (b.p. 80°–100° C/0.04 Torr) in a manner analogous to that employed in Example 7(a), and reacting this latter with 1-ethyl-2-(aminomethyl)-pyrrolidine as in Example 7(b).

EXAMPLE 9

18.1 g (0.1 mole) of 2-methoxy-4,6-dimethylnicotinic acid together with 12.8 g (0.1 mole) of 1-ethyl-2-(aminomethyl)-pyrrolidine and 31 g (0.1 mole) of triphenylphosphite are dissolved in 400 ml of toluene. The reaction mixture is refluxed for 5 hours, cooled, and extracted with two 100 ml portions of 2 N hydrochloric acid.

The acid aqueous phases are made alkaline with concentrated sodium hydroxide solution, saturated with potassium carbonate and extracted with benzene. The benzene phases are dried over magnesium sulphate and then evaporated to dryness.

The residue is dissolved in benzene and purified by filtration through a column of 50 g of basic silica gel.

The eluates are evaporated to dryness and the residual base is dissolved in acetone. After addition of an ethereal solution of hydrochloric acid until the onset of acid reaction to Congo red, the precipitated hydrochloride is collected by filtration and recrystallised from absolute ethanol-ether. The N-[(1-ethyl-2-pyrrolidinyl)-methyl]-2-methoxy-4,6-dimethylnicotinamide hydrochloride obtained melts at 225°–229° C.

N-[(2-quinuclidinyl)-methyl]-2,6-dimethoxynicotinamide hydrochloride, with a melting point of 136°–139° C, is obtained in analogous manner starting from 18.3 g (0.1 mole) of 2,6-dimethoxynicotinic acid, 15.4 g (0.11 mole) of 2-(aminomethyl)-quinuclidine [prepared according to the method of M. V. Rubtsov et al., Zhur. Obschei Khim, 23, 1555–1559 (1953); C.A. 48, 12114i (1954)] and 31 g (0.1 mole) of triphenylphosphite in 150 ml of toluene.

The 2-methoxy-4,6-dimethylnicotinic acid required as first starting material is obtained as follows:

97 g (0.6 mole) of 2-methoxy-4,6-dimethylnicotinonitrile and 230 g of solid potassium hydroxide are dissolved in 1000 ml of ethanol and 120 ml of water and the solution is refluxed under nitrogen for 82 hours. The mixture is cooled, the precipitated substance collected by filtration, and the bulk of the ethanol is distilled off from the filtrate in vacuo. The residue is dissolved in 500 ml of water and extracted with methylene chloride. The alkaline aqueous phase is adjusted to pH 3.3 with concentrated hydrochloric acid and the precipitated crude product is collected by filtration. Recrystallisation of this crude product from ethanol yields pure 2-methoxy-4,6-dimethylnicotinic acid (m.p. 210°–215° C).

EXAMPLE 10

By carrying out the procedure described in Example 9, N-(3-quinuclidinyl)-2,6-dimethoxynicotinamide hydrochloride with a melting point of 203°–205° C, is obtained from 18.3 g (0.1 mole) of 2,6-dimethoxynicotinic acid, 15 g (0.12 mole) of 3-aminoquinuclidine and 31 g (0.1 mole) of triphenylphosphite.

EXAMPLE 11

16 g of imidazole (0.25 mole) are dissolved in 100 ml of tetrahydrofurane and 7.2 g (0.06 mole) of thionyl chloride are added dropwise at 10° C. After completion of addition, the temperature is allowed to rise to 20° C and the mixture is left to stand for 30 minutes.

Then 9.15 g (0.05 mole) of finely powdered 2,6-dimethoxynicotinic acid are added at room temperature and the mixture is heated for 1 hour to 50° C.

After cooling once more to 20° C, 12 g (0.12 mole) of triethylamine are added dropwise and the temperature is kept for 1 hour at 50° C. The mixture is then cooled to 20° C and 6.4 g (0.05 mole) of 1-methyl-2-(aminomethyl)-piperidine (prepared in accordance with German Offenlegungsschrift 1,620,229) are slowly added dropwise. The reaction mixture is heated for 2 hours to 50° C. Thereafter the substance is collected by filtration and the filtrate is evaporated to dryness in vacuo.

The residue is dissolved in 100 ml of water, the solution saturated with potassium carbonate and extracted three times with ether. The ethereal solutions are extracted with three 50 ml portions of a 1 molar aqueous solution of sodium dihydrogen citrate, the aqueous phases made alkaline with concentrated sodium hydroxide solution and, after saturation with potassium carbonate, extracted three times with ether. The ethereal solutions are dried over magnesium sulfate and evaporated to dryness in vacuo. The residue is distilled in a high vacuum to yield pure N-[(1-methyl-2-piperidinyl)-methyl]-2,6-dimethoxynicotinamide with a boiling point of 205°–210° C/0.05 Torr as a yellowish oil.

The (1:1)-maleate prepared in a manner analogous to that described in Example 14 melts at 113°–116° C.

EXAMPLE 12

15 g (0.05 mole) of N-[(1-ethyl-2-pyrrolidinyl)-methyl]-2-methoxy-6-chloronicotinamide are dissolved in 200 ml of methanol and catalytic hydrogenation is effected with the addition of 1.5 g of palladium carbon (5%) at room temperature and a hydrogen pressure of 2 bar. The uptake of hydrogen is complete after approx. 90 minutes. The catalyst is subsequently removed by filtration, the filtrate evaporated to dryness and the residue dissolved in 2 N hydrochloric acid. The acid aqueous solution is extracted with benzene and thereafter made alkaline with concentrated sodium hydroxide solution, saturated with potassium carbonate, and once more extracted with benzene. The benzene solutions are combined, dried over magnesium sulphate, concentrated to dryness in vacuo, and the residual crude product in the form of an oil is distilled in a high vacuum.

The pure N-[(1-ethyl-2-pyrrolidinyl)-methyl]-2-methoxynicotinamide boils at 170°–175° C/0.01 Torr.

EXAMPLE 13

The following compounds are prepared by carrying out the procedure described in Example 1:

N-[(1-ethyl-2-pyrrolidinyl)-methyl]-2-methoxy-6-(methylthio)-nicotinamide, starting from 2.13 g (0.010 mole) of methyl 2-methoxy-6-(methylthio)-nicotinate and 1.8 g (0.015 mole) of 1-ethyl-2-(aminomethyl)-pyrrolidine in 15 ml of xylene; and N-[(1-ethyl-2-pyrrolidinyl)-methyl]-2-methoxy-6-(methylsulphonyl)-nicotinamide, starting from 2.45 g (0.010 mole) of methyl 2-methoxy-6-(methylsulphonyl)-nicotinate and 1.8 g (0.015 mole) of 1-ethyl-2-(aminomethyl)-pyrrolidine in 15 ml of xylene.

The substituted methyl nicotinates required as starting materials are obtained as follows:

(a) To 10 ml of a 1 N methanolic sodium methoxide solution are added dropwise 3 ml of a 3.5 N methanolic methylmercaptan solution. To the resultant methylmercaptide solution is added a solution of 2.01 g (0.01 mole) of methyl 2-methoxy-6-chloronicotinate (cf. Example 6 a)) in 30 ml of methanol. The reaction mixture is refluxed for 5 hours and the solvent is thereafter evaporated in vacuo. The residue is treated with 30 ml of saturated potassium carbonate solution and 150 ml of methylene chloride and separated in a separating funnel. The methylene chloride solution is dried over sodium sulphate and subsequently evaporated to dryness in vacuo. The crystallised residue is recrystallised from pentane and yields the methyl 2-methoxy-6-(methylthio)-nicotinate with a melting point of 71°–75° C.

(b) 3.8 g (0.20 mole) of 90% m-chloro-peroxybenzoic acid are added at 5°–10° C to a solution of 2.13 g (0.010 mole) of of methyl 2-methoxy-6-(methylthio)-nicotinate. The reaction mixture is stirred for 5 hours at room temperature and then 25 ml of saturated sodium carbonate solution are added. The layers are separated and the methylene chloride solution is evaporated in vacuo. The crystallised residue is recrystallised from methylene chloride-hexane to yield methyl 2-methoxy-6-(methylsulphonyl)-nicotinate with a melting point of 88°–90° C.

EXAMPLE 14

29.3 g (0.1 mole) of N-[(1-ethyl-2-pyrrolidinyl)-methyl]-2,6-dimethoxynicotinamide are dissolved in 200 ml of ethyl acetate and to this solution is added a solution of 11.6 g (0.1 mole) of maleic acid in 50 ml of hot acetone. The precipitated product is collected by filtration and recrystallised from absolute ethanol-ether. The resultant N-[(1-ethyl-2-pyrrolidinyl)-methyl]-2,6-dimethoxynicotinamide maleate-(1:1) melts at 115°–117° C.

What we claim is:

1. A basically substituted pyridine carboxamide of the formula I

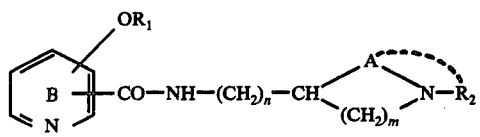

wherein
R$_1$ represents lower alkyl and —OR$_1$ is in the adjacent position to the carboxamide group,
R$_2$ represents lower alkyl or an ethylene radical which is attached to one of the trivalent radicals designated as A and the nitrogen atom located between it to form a 6-membered ring,
A represents a divalent saturated aliphatic hydrocarbon radical which contains not more than 7 carbon atoms and whose two linkage positions are separated by (3-$m$) to 4 carbon atoms, or, if R$_2$ is an ethylene radical, represents the 1-propanyl-3-ylidene radical, if $m$ is 1, or the 1,2,4-butane-triyl radical, if $m$ is 0,
and one of the factors $m$ and $n$ is 0 and other is 1, and the ring B is substituted only by O—R$_1$ or additionally by halogen with an atomic number up to 35, by lower alkyl, lower alkoxy, lower alkylthio, lower alkylsulphinyl, lower alkylsulphonyl, di-lower alkylamino or cyano, and the acid addition salts thereof.

2. A compound according to claim 1 having the formula I in which R$_1$, R$_2$, $m$ and $n$ are as defined in claim 1 and A represents trimethylene or, if R$_2$ is an ethylene radical, represents the 1-propanyl-3-ylidene radical, if $m$ is 1, or the 1,2,4-butane-triyl radical, if $m$ is 0, and, if desired, the ring B is substituted only by O—R$_1$ or additionally as defined in claim 1, and the acid addition salts thereof.

3. A compound according to claim 1 having the formula I given in claim 1, in which R$_1$, R$_2$, $m$ and $n$ are as defined in claim 1 and A represents trimethylene or, if R$_2$ is an ethylene radical, represents the 1-propanyl-3-ylidene radical, if $m$ is 1, or the 1,2,4-butane-triyl radical, if $m$ is 0, and the ring B is substituted only by O—R$_1$ or additionally by halogen with an atomic number up to 35, by lower alkyl, lower alkoxy, lower alkylthio, lower alkylsulphinyl or lower alkylsulphonyl, and the acid addition salts thereof.

4. A compound according to claim 1 having the formula I given in claim 1, in which R$_1$ represents lower alkyl, R$_2$ represents lower alkyl, and A represents trimethylene, $m$ and $n$ are as defined in claim 1 and the ring B is substituted only by O—R$_1$ or additionally by halogen with an atomic number up to 35, by lower alkyl, lower alkoxy, lower alkylthio, lower alkylsulphinyl or lower alkylsulphonyl, and the acid addition salts thereof.

5. A compound according to claim 1 having the formula I given in claim 1, in which R$_1$ represents methyl, R$_2$ represents ethyl, A represents trimethylene, $m$ is 0 and $n$ is 1, and the ring B is substituted only by O—R$_1$ or additionally by chlorine, methyl or methoxy, and the pharmaceutically acceptable acid addition salts thereof.

6. A compound according to claim 1 which is N-[(1-ethyl-2-pyrrolidinyl)-methyl]-4-methoxynicotinamide, and the pharmaceutically acceptable acid addition salts thereof.

7. A compound according to claim 1 which is N-[(1-ethyl-2-pyrrolidinyl)-methyl]-3-methoxypicolinamide, and the pharmaceutically acceptable acid addition salts thereof.

8. A compound according to claim 1 which is N-[(1-ethyl-2-pyrrolidinyl)-methyl]-3-methoxy-6-methylpicolinamide, and the pharmaceutically acceptable salts thereof.

9. A compound according to claim 1 which is N-[(1-ethyl-2-pyrrolidinyl)-methyl]-2,6-dimethoxynicotinamide, and the pharmaceutically acceptable acid addition salts thereof.

10. A compound according to claim 1 which is N-[(1-ethyl-2-pyrrolidinyl)-methyl]-2-methoxy-6-chloronicotinamide, and the pharmaceutically acceptable acid addition salts thereof.

11. A compound according to claim 1 which is N-[(2-quinuclidinyl)-methyl]-2,6-dimethoxynicotinamide, and the pharmaceutically acceptable salts thereof.

12. A compound according to claim 1 which is N-(3-quinuclidinyl)-2,6-dimethoxynicotinamide, and the pharmaceutically acceptable acid addition salts thereof.

13. An antiemetic, psychosomatic and antipsychotic pharmaceutical composition comprising a therapeutically effective amount of a compound according to claim 1 and having the formula I

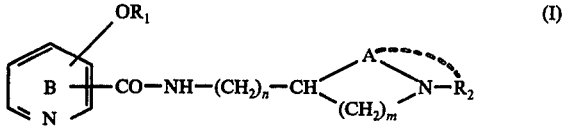

in which R$_1$, R$_2$, A, $m$ and $n$ are as defined in claim 1 and, the ring B is substituted only by O—R$_1$ or additionally as defined in claim 1, or of a pharmaceutically acceptable acid addition salt thereof, together with a solid, powdery carrier or a suppository base.

14. A pharmaceutical composition according to claim 13 wherein a therapeutically effective amount of a compound having the formula I given in claim 13, in which R$_1$ represents lower alkyl and —OR$_1$ is in the adjacent position to the carboxamide group, R$_2$ represents lower alkyl or an ethylene radical which is attached to one of the trivalent radicals designated as A and the nitrogen atom located between it to form a 6-membered ring, A represents trimethylene or, if R$_2$ is an ethylene radical, represents the 1-propanyl-3-ylidene radical, if $m$ is 1, or the 1,2,4-butane-triyl radical, if $m$ is 0, one of the factors $m$ and $n$ is 0 and the other is 1, and the ring B is substituted only by O—R$_1$ or additionally by halogen with an atomic number up to 35, by lower alkyl, lower alkoxy, lower alkylthio, lower alkylsulphinyl, lower alkylsulphonyl, di-lower alkylamino or cyano, or of a pharmaceutically acceptable acid addition salt thereof is present.

15. A pharmaceutical composition according to claim 13 wherein a therapeutically effective amount of a compound of having the formula I given to claim 13, in which $R_1$ represents methyl, $R_2$ represents ethyl, A represents trimethylene, $m$ is 0 and $n$ is 1, and the ring B is substituted only by O—$R_1$ or additionally by chlorine, methyl or methoxy, or of a pharmaceutically acceptable acid addition salt thereof is present.

16. A pharmaceutical composition according to claim 13, wherein a therapeutically effective amount of N-[(1-ethyl-2-pyrrolidinyl)-methyl]-2,6-dimethoxynicotinamide or of a pharmaceutically acceptable acid addition salt thereof is present.

17. A method for the treatment of a state of psychomotor excitation in a warmblooded animal comprising administration to said animal of a therapeutically effective amount of a compound according to claim 1 and having the formula I

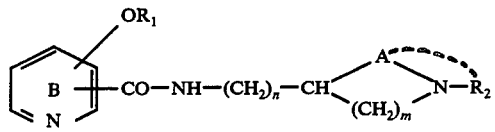

(I)

in which $R_1$, $R_2$, A, $m$ and $n$ are as defined in claim 1 and, the ring B is substituted only by O—$R_1$ or additionally as defined in claim 1, or of a pharmaceutically effective acid addition salt thereof.

18. A method according to claim 17 comprising administration of a therapeutically effective amount of a compound having the formula I given in claim 17, in which $R_1$ represents lower alkyl and —$OR_1$ is in the adjacent position to the carboxamide group, $R_2$ represents lower alkyl or an ethylene radical which is attached to one of the trivalent radicals designated as A and the nitrogen atom located between it to form a 6-membered ring, A represents trimethylene or, if $R_2$ is an ethylene radical, represents the 1-propanyl-3-ylidene radical, if $m$ is 1, or the 1,2,4-butane-triyl radical, if $m$ is 0, one of the factors $m$ and $n$ is 0 and the other is 1, and the ring B is substituted only by O—$R_1$ or additionally by halogen with an atomic number up to 35, by lower alkyl, lower alkoxy, lower alkylthio, lower alkylsulphinyl, lower alkylsulphonyl, di-lower alkylamino or cyano, or of a pharmaceutically acceptable acid addition salt thereof.

19. A method according to claim 17 comprising administration of a therapeutically effective amount of a compound having the formula I given in claim 17, in which $R_1$ represents methyl, $R_2$ represents ethyl, A represents trimethylene, $m$ is 0 and $n$ is 1, and the ring B is substituted only by O—$R_1$ or additionally by chlorine, methyl or methoxy, or of a pharmaceutically acceptable acid addition salt thereof.

20. A method according to claim 17 comprising administration of a therapeutically effective amount of N-[(1-ethyl-2-pyrrolidinyl)-methyl]-2,6-dimethoxynicotinamide or of a pharmaceutically acceptable acid addition salt thereof.

21. An antiemetic, psychosomatic and antipsychotic pharmaceutical composition for parenteral administration which is an aqueous solution of a therapeutically effective amount of a water-soluble, pharmaceutically acceptable acid addition salt of a compound according to claim 1 having the formula I given in claim 1, in which $R_1$, $R_2$, A, $m$ and $n$ are as defined in claim 1 and the ring B is substituted only by O—$R_1$ or additionally as defined in claim 1.

* * * * *